United States Patent [19]

Marsoner

[11] 4,264,328
[45] Apr. 28, 1981

[54] METHOD FOR RECORDING MEASURED VALUES IN AN AUTOMATICALLY PERFORMED BLOOD GAS ANALYSIS

[75] Inventor: Hermann Marsoner, Graz, Austria
[73] Assignee: AVL AG, Schaffhausen, Switzerland
[21] Appl. No.: 961,431
[22] Filed: Nov. 16, 1978
[30] Foreign Application Priority Data
Nov. 16, 1977 [CH] Switzerland .......... 14015/77
[51] Int. Cl.³ ............ G01N 33/48; G01N 27/26
[52] U.S. Cl. ................... 23/230 B; 23/928; 204/1 T; 346/33 ME
[58] Field of Search ............ 23/230 B, 928; 422/68; 324/30 R; 346/33 ME; 364/497; 204/1 T

[56] References Cited

U.S. PATENT DOCUMENTS 3,763,422 10/1973 MacPhee et al. .......... 23/928
3,874,850 4/1975 Sorensen et al. .......... 23/230 B

OTHER PUBLICATIONS

Lab. Equip. Dig., vol. 14, No. 3, pp. 83, 85, 87, 89, 91 and 92, Mar. 1976, Pub. Gerard Mann Ltd. 1-3 Astoria Parade, Streatham High Road, London, SW16, PP England.

Primary Examiner—R. E. Serwin
Attorney, Agent, or Firm—Ladas & Parry

[57] ABSTRACT

The measured values are calculated from the following equation:

$$X_2 = \frac{X_i \cdot X_{i+2} - (X_{i+1})^2}{X_i + X_{i+2} - 2 \cdot X_{i+1}}$$

in which $X_1$, $X_{i+1}$, $X_{i+2}$ are three values of signals obtained from one electrode measured successively at equal intervals of time, namely after a latent time $\tau$ has elapsed.

The time required for calibration and measurement in the course of a blood gas analysis can be substantially reduced by the consistent application of this procedure for obtaining the measured value for each calibration and measurement.

3 Claims, 1 Drawing Figure

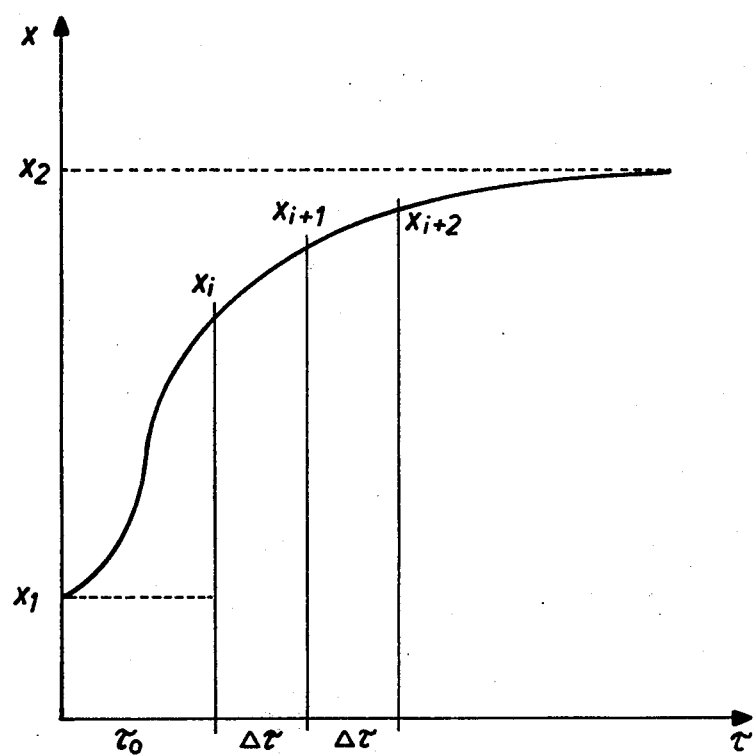

METHOD FOR RECORDING MEASURED VALUES IN AN AUTOMATICALLY PERFORMED BLOOD GAS ANALYSIS

The present invention relates to a method for obtaining measured values in blood gas analysis from signals supplied by the relevant measuring electrode when it changes from one of its equilibrium states into another.

The term blood gas analysis generally refers to the simultaneous recording of the small pH value and of the partial pressures of oxygen and $CO_2$ in a blood specimen. Generally this is performed in a measuring cell, for example as described in the Austrian Patent Application No. 6A 1954/75-2, in which a series of selective electrodes are inserted for the three parameters that are to be measured and that these selective electrodes are used for determining the above-mentioned measured values. The said selective electrodes are connected to an analysis instrument which displays the recorded measured values.

The process of performing blood gas analysis is divided into three methodic phases:
1. Determining the characteristic calibration values of the electrodes, also briefly referred to as calibration,
2. Maintaining the measuring standby condition,
3. Performing the actual measurement.

The actual measurement is performed by the specimen, contained either in a thin capillary glass tube or in a conventional syringe, being attached to a specimen inlet part whereupon it is automatically drawn into the measuring cell after a switch element is actuated by an operator.

In this procedure it is essential to obtain recognition as to whether an adequate quantity of specimen material is contained in the analysis cell or measuring cell.

After recording the values of the signals delivered by the electrodes the corresponding measured values are calculated with the aid of appropriate calibration values in accordance with known procedures and are displayed.

The manner in which the equilibrium signal values of the electrodes are determined is essential for performing calibration and measurement. Stable equilibrium values in contact with a calibrating gas or with a specimen are obbtained only relatively slowly by electrochemical measuring probes in general and by electrodes for blood gas analysis in particular. This is due to the fact that a series of successive phenomena of diffusion and chemical or electrochemical reactions take place and must achieve a fresh equilibrium when changing from one stable condition into another. It is common practice to use the measuring instruments which employ electrochemical electrodes for determining the stable equilibrium signal, to test whether the change of signal per unit time drops below a specific amount. The signal which occurs at the time at which the rate of change of signal drops below the specified value is regarded as the equilibrium signal and taken as the measured value. In known analyzers this calls for a relatively long waiting time until an equilibrium value is obtained. The disadvantage of an unreliable measured result occurs in addition to the above-mentioned disadvantage of the long measuring period since drift phenomena, resulting from secondary effects, could occur during the setting up procedure.

It is the object of the present invention to eliminate these disadvantages.

This is achieved by the method according to the invention which is characterised in that the signals of the electrode are recorded after a latent phase so that the time interval between the interrogation of two successive measured values of the same electrode are of equal length and that the desired result value is calculated from these three successive values obtained by such above described interrogation.

One embodiment of the present invention will be explained hereinbelow by reference to the accompanying drawing.

To understand the present procedure more readily it is necessary to mention various features regarding the previously-mentioned phases of blood gas analysis and the technological means for performing such analysis.

An assembly, comprising a pH sensitive gas electrode and a reference electrode is normally used to measure the pH value of a blood specimen. The sensitive part of the pH sensitive gas electrode is disposed in a measuring cell so that it can be brought into contact with the specimen. The reference electrode, which has no pH sensitivity, communicates with the specimen in the measuring cell by means of an electrolytic contact. A reference electrode system of this kind was described, for example, in the Austrian Patent No. 321 868. Contact of this electrode system with a specimen results in an electric voltage difference between the two electrodes, which said voltage difference is proportional to the pH value of the specimen. Since there is a linear relationship between the generated electric voltage difference and the pH value over a wide pH range in such electrode system it follows that a calibration characteristic of the electrode system can be determined by successively bringing it into contact with two buffer solutions having a different pH value and by measuring the corresponding voltage differences on the electrodes. If the calibration characteristics is known, it will then be possible to determine an unknown pH value of a specimen by measuring the voltage on such electrodes.

A $CO_2$ sensitive electrode, of the kind described, for example, by Stow and his collegues in Archiv für physikalische Medizin und Rehabilitation, Volume 38 (1957) is used for measuring the partial pressure of $CO_2$ ($PO_2$) dissolved in blood. In contact with a liquid or a gas having a specified $CO_2$ content an electrode of this kind will generate an electric voltage which is proportional to the logarithm of the $PCO_2$ value. A calibration characteristic is also defined for this electrode. This is achieved by successively contacting the electrode with two gases having a different $CO_2$ content (preferably approximately 5% and 10% $CO_2$) and by measuring the electric voltage generated on the electrode.

A sensitive electrode for measuring oxygen in a liquid or gaseous specimen was described for the first time by Clark in the Journal of Applied Physiology, Volume 6 (1953). The electrode system described therein for measuring the oxygen by means of the polarographic method is generally employed to the present day in various constructions. Reduction of oxygen molecules, which reach the electrode by diffusion through an oxygen permeable diaphragm, produces an electric current flow in the electrode, which said current flow is proportional to the diffusion flow of oxygen molecules to the electrode and under certain conditions it is therefore proportional to the partial pressure of oxygen in the specimen. Due to a series of secondary electrochemical processes there will however also be a very small residual current flow on the electrode when this is in contact with a medium which is free of oxygen. Generally, this residual current is determined for a specific electrode by means of a gas which is free of oxygen. This again provides one point of a calibration characteristic. The second calibrating point is determined by means of a gas having a specific oxygen content (preferably 20% oxygen). An unknown partial oxygen pressure can again be determined by measurement of the electrode current, if the calibration characteristic is known, as in the above-described electrodes.

An analysis instrument for performing blood gas analysis and connected to the above-mentioned electrodes comprises the following modules:

(A.) A measuring chamber for retaining the above-mentioned electrodes and in which the sensitive parts thereof can be brought into contact with the calibration gases, the calibration buffer solutions and the specimens. The specimen space of such a measuring chamber, for example of the kind described in the Austrian Patent No. 6A1954/75-2 consists of insulating material. Since the absolute blood gas measured values depend on the temperature at which measurement is performed, the measuring cell of a blood gas analyzer is provided with a thermostat device by means of which measurement is performed more particularly at a temperature of 37° C. To maintain a constant temperature in some embodiments a heated water jacket surrounds the specimen chamber of insulating material. In other embodiments and more particularly in the device described herein for performing the present method the specimen chamber is surrounded by a heated and temperature controlled metal member.

(B.) To calibrate the electrodes and to carry out measurements calls for devices which permit the measuring cell to be charged with calibrating gases, calibrating buffer solutions and specimens and enable the electrodes to be brought into contact with these media. This function is performed in different ways in known blood gas analyzers. In a preferred embodiment this function is performed by the input and output of the measuring cell being closely associated with a rotatable ring, the periphery of which is provided with a series of connections which can be made to optionally communicate with the input or output of the measuring cell by rotation of the ring. This enables the connections between input and output of the measuring cell and other components of the analysis apparatus, as listed in the table below, to be established.

| INPUT | OUTPUT |
| --- | --- |
| Specimen input device | Peristaltic pump |
| Storage vessel for the 1st buffer solution | Peristaltic pump |
| Storage vessel for the 2nd buffer solution | Peristaltic pump |
| Storage vessel for the washing water | Suction pump |
| Open | Suction pump |
| Device for preparing the 1st and 2nd calibrating gas | Open |
| Device for preparing the 3rd calibrating gas | Open |

(C.) Connections between the input and output of the measuring cell and other components of the analysis apparatus.

(D.) A device for preparing calibrating gases. In many cases, calibrating gases, having a defined concentration of oxygen and $CO_2$ and contained in tanks, are supplied to the analyzer. However, devices, more particularly those disclosed in the Austrian Patent No. 300 423, are available by means of which calibrating gases for blood gas analyzers can be prepared from simple and primary gases (for example air and pure $CO_2$). Three calibrating gases comprising air and pure $CO_2$ are prepared by means of a device in accordance with the above-mentioned Austrian Patent for the preferred embodiment of an analyzer. The approximate composition of these calibrating gases is shown in the table below.

Composition of calibrating gases for blood gas analysis:

| No. | $CO_2$ | $O_2$ |
| --- | --- | --- |
| 1 | 5.5% | 19.9% |
| 2 | 11% | 18$\frac{1}{6}$6% |
| 3 | 100% | — |

(E.) Means for cleaning the analysis cell after measurement and for introducing the specimen into the said cell. Means of this kind are described in an article by Grabow entitled "Eine Elektrodenanordnung für schnelle Blutgasanalysen" published in the journal "Der Anästhesist", Volume 15 (1966).

(F.) Electronic means for controlling the analysis procedure and for measuring the electrical signals of the electrodes, for storing the characteristic calibration values and for calculating the measured values of a specimen from the signals of the electrode and for calculating the characteristic calibrating value obtained from a preceding calibration.

It was already mentioned initially that blood gas analysis is divided into three phases.

A calibrating procedure in turn is further subdivided into the following steps described below:

(a) Determining the zero signal of the oxygen electrode; this signal is provided by the electrode current obtained when the electrode in the measuring cell is in contact with the calibrating dimension 3.

(b) Determining the value of the voltage of the pH electrode system in contact with the calibration buffer 2. This calibration is performed several times in succession to check whether the same calibration value is reproducibly obtained with sufficiently low differences.

(c) Determining the value of the voltage on the pH electrode system in contact with the calibration buffer 1. This step is also performed several times to check the reproducibility.

(d) Determining the value of the voltage on the $CO_2$ electrode in contact with the calibrating gas 2.

(e) Determining the value of the voltage of the $CO_2$ electrode and the value of the current of the $PO_2$ electrode when both electrodes are in contact with the calibrating gas 1.

In each of these procedures a check is made whether the values obtained are within predefined limits. Steps are also taken to determine whether the reproducibility of the values is ensured within specific defined tolerances. A corresponding warning signal is provided if one of these conditions is not satisfied.

The standby condition of the analyzer is obtained if the storage vessels for the calibration buffer solutions, for the electrolyte solution of the reference electrode, the vessels for the washing water of the measuring cell and the waste water of the measuring cell have corresponding levels. These levels are continuously monitored at specific times and warning signals are triggered if the predefined levels are exceeded or not reached. The presence of the required calibrating gases is also monitored. Warning signals come into operation in the event of pressure loss in the calibration gas ducts. To maintain the standby condition it is also necessary for the calibrating gas 1 to flow constantly through the measuring cell and that the signals of the $PCO_2$ and $PO_2$ electrodes are constantly measured and stored. Warning signals are again triggered if these values move outside specific predefined limits due to drift.

As already mentioned, measurement is performed by the specimen, contained either in a thin capillary glass tube or in a conventional syringe, being attached to the specimen inlet part of an analysis apparatus and thereafter the specimen is automatically drawn into the measuring cell after a switch element is actuated by the operator. The corresponding measured values are calculated by known methods with the aid of known calibration values and are displayed after determining the values of the signals delivered by the electrodes.

As already mentioned the manner of determining the signals characterising the appropriate state of equilibrium of the measuring electrode is central for performing calibration and measurement. To determine the stable equilibrium signal a check is normally made in measuring instruments with electrochemical electrodes to determine whether the change of signal per unit time drops below a specific amount. The time at which the rate of change of a predefined signal drops below the specified value is regarded as the equilibrium signal delivered by the electrode and is taken as the required measured value.

The curve shown in the accompanying drawing shows the characteristic of a signal X, delivered by an electrode, plotted against the time $\tau$.

If the electrode changes from one equilibrium state to a fresh equilibrium state the signal delivered by this electrode will change as indicated by the following equation:

$$X = X_2 - (X_1 - X_2) \cdot I^{\Sigma - a_i \tau} \tag{1}$$

This equation points to an additive superimposition of a number of exponential setting procedures. After a latent phase $\tau_o$ has elapsed the major part of the components of the setting procedure will have decayed to the extent that the remaining characteristic of this setting procedure can be described as a single exponential function by means of the following expression:

$$X = X_2 - (X_1 - X_2) \cdot \rho^{-a\tau} \tag{2}$$

It has been found that the final value corresponding to the new equilibrium state of the electrode can be calculated by means of the following equation:

$$X_2 = \frac{X_i \cdot X_{i+2} - (X_{i+1})^2}{X_i + X_{i+2} - 2 \cdot X_{i+1}} \tag{3}$$

In this equation $X_i$, $X_{i+1}$ and $X_{i+2}$ refer to three individual measured values obtained after the latent time $\tau_o$ has elapsed and between each of which there is a time interval $\Delta \tau$.

The time required for calibration and for measurement can be substantially reduced by the consistent application of this procedure for determining the measured values.

I claim:

1. Method for obtaining a result value in blood gas analysis from a signal supplied by a measuring electrode when it changes from one equilibrium state into another, wherein the signal is measured after a latent phase ($\tau_o$) following the beginning of the change from said one equilibrium state to the other equilibrium state to provide a first measured value ($X_i$), the signal is measured after an interval following the first measurement to provide a second measured value ($X_{i+1}$), the signal is measured after an interval following the second measurement to provide a third measured value ($X_{i+2}$) and the result value is calculated from the three measured values, the inerval ($\Delta \tau$) between the second and third measurements being substantially equal to the interval ($\Delta \tau$) between the first and second measurements.

2. Method according to claim wherein 1, the result value is calculated in accordance with the following equation:

$$X_2 = \frac{X_i \cdot X_{i+2} - (X_{i+1})^2}{X_i + X_{i+2} - 2 \cdot X_{i+1}}$$

where $X_i$, $X_{i+1}$, $X_{i+2}$ represent the three successive values measured.

3. Method according to claim 1, wherein a gaseous or liquid medium is brought into contact with electrochemical electrodes before the signals are recorded, the time of complete contact of the electrodes with a liquid specimen is recognized and whether a sufficient specimen quantity is present is also recognized.

* * * * *